United States Patent
Oladipo

(10) Patent No.: US 6,595,936 B1
(45) Date of Patent: Jul. 22, 2003

(54) ARM SUPPORT GARMENT

(76) Inventor: Olarewaju J. Oladipo, P.O. Box 446, Canton, MA (US) 02021

( * ) Notice: Subject to any disclaimer, the term of this patent is extended or adjusted under 35 U.S.C. 154(b) by 0 days.

(21) Appl. No.: 09/605,963

(22) Filed: Jun. 28, 2000

(51) Int. Cl.[7] .................................................. A61F 5/00
(52) U.S. Cl. .............................. 602/4; 602/5; 602/20; 602/21
(58) Field of Search .............................. 602/4–5, 60–62, 602/75–77, 20–21; 128/878–880

(56) References Cited

U.S. PATENT DOCUMENTS

| | | | |
|---|---|---|---|
| 4,601,285 A | | 7/1986 | Whitchurch .................. 128/94 |
| 5,095,894 A | * | 3/1992 | Marble |
| D381,429 S | | 7/1997 | Millwood ................... D24/190 |
| 5,772,617 A | | 6/1998 | Lay ................................. 602/4 |
| 5,792,083 A | | 8/1998 | Joslin ............................. 602/4 |

OTHER PUBLICATIONS

Sammons Preston Rehabilitation Supplies Catalog.
Freeman Orthotics and Prosthetics Catalog.

* cited by examiner

*Primary Examiner*—Nicholas D. Lucchesi
*Assistant Examiner*—Lalita M Hamilton
(74) *Attorney, Agent, or Firm*—Weingarten, Schurgin, Gagnebin & Lebovici LLP

(57) ABSTRACT

An arm support garment with an integral arm sling pouch for comfortably supporting and immobilizing the upper extremity on either the inner or outer surfaces of the front of the garment is disclosed. The sling pouch in the garment of the invention is accessed from the front exterior portion of the garment through vertical slits oriented in the garment material near each end of the pouch. Additional slits may also be provided to aid in ventilation. The pouch is preferably made with an expandable inside layer to allow usage by individuals with different forearm sizes. A separate support pouch of this configuration can also be used with traditional arm slings.

7 Claims, 5 Drawing Sheets

ARM SUPPORT GARMENT

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

In current orthopedic practice, sling devices to support the shoulder, forearm, wrist and hand following the occurence of an injury are worn with the forearm supported in an exterior position relative to, and typically separate from, the patient's clothing. Such slings are typically equipped with numerous adjustable straps and buckles.

BRIEF SUMMARY OF THE INVENTION

The present invention relates to an arm support garment with an integral arm sling pouch for comfortably supporting and immobilizing the upper extremity on either the inner or outer surfaces of the front of the garment. The sling pouch in the garment of the invention is accessed from the front exterior portion of the garment through vertical slits oriented in the garment material near each end of the pouch. Additional slits may also be provided to aid in ventilation and serve as additional access openings. The pouch is preferably made with an expandable inside layer to allow usage by individuals with different forearm sizes. A separate support pouch of this configuration can also be used with traditional arm slings.

The arm support garment, which is preferably in the form of a T-shirt or a vest, is generally made from a material, e.g., a heavy cotton, with limited stretch capacity to resist the deforming effect of the weight of the forearm on the material of the clothing. Alternatively, additional support can be provided on the inside of the garment in the form of sewn-in over-the-shoulder support straps.

With traditional arm slings, the entire weight of the upper extremity is supported by the neck. The arm support garment of the invention allows this weight to be spread throughout the garment so as to be distributed over the shoulders of the patient. Additionally, keeping the supported extremity on an inside pouch, as in this invention, supports the injured extremity close to the chest as is usually desired for optimum immobilization, e.g., after a shoulder dislocation. Overall application of this garment is easy, particularly by a patient with an injured extremity. It takes same effort as putting on a standard article of clothing as the supporting pouch needs none of the numerous straps and buckles of existing devices.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Figure 1:
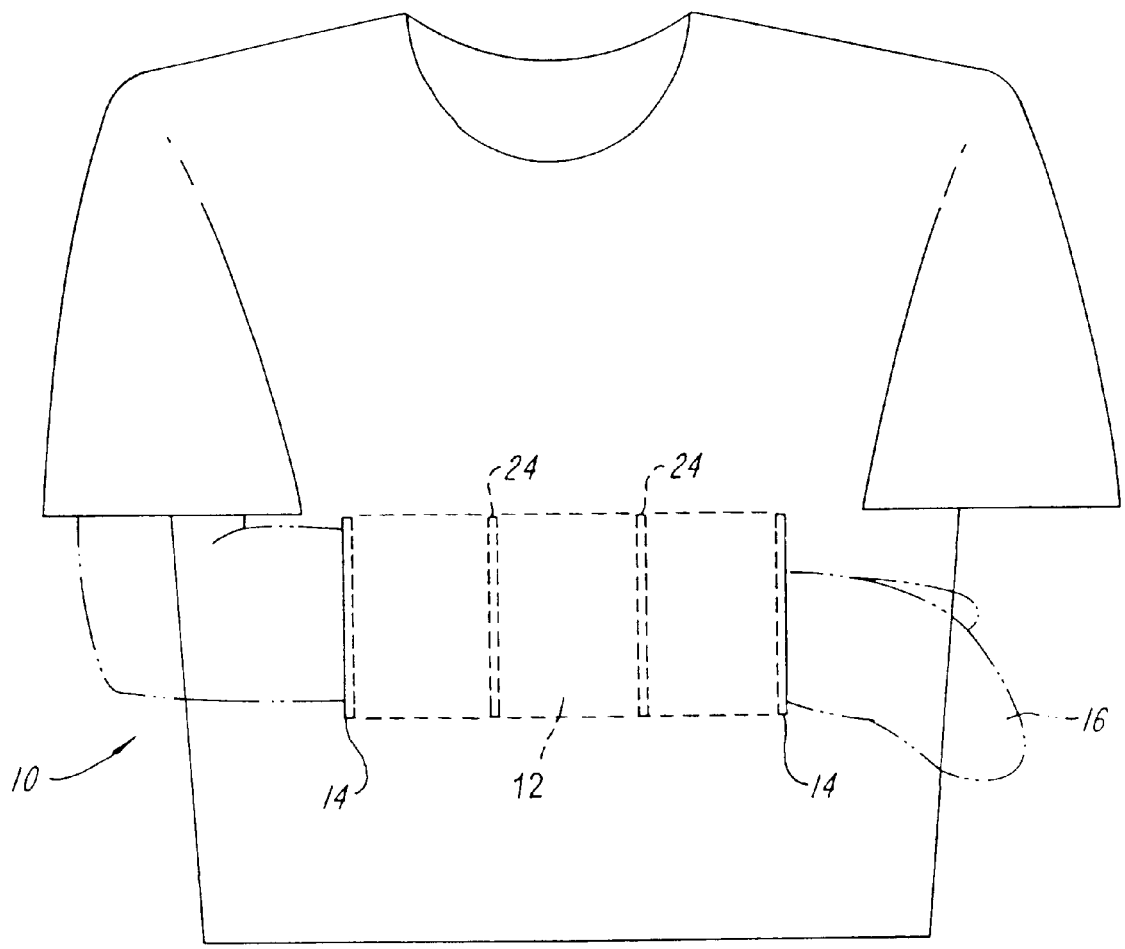
FIG. 1 is a front exterior perspective view of the arm support garment of the invention.
Figure 2:
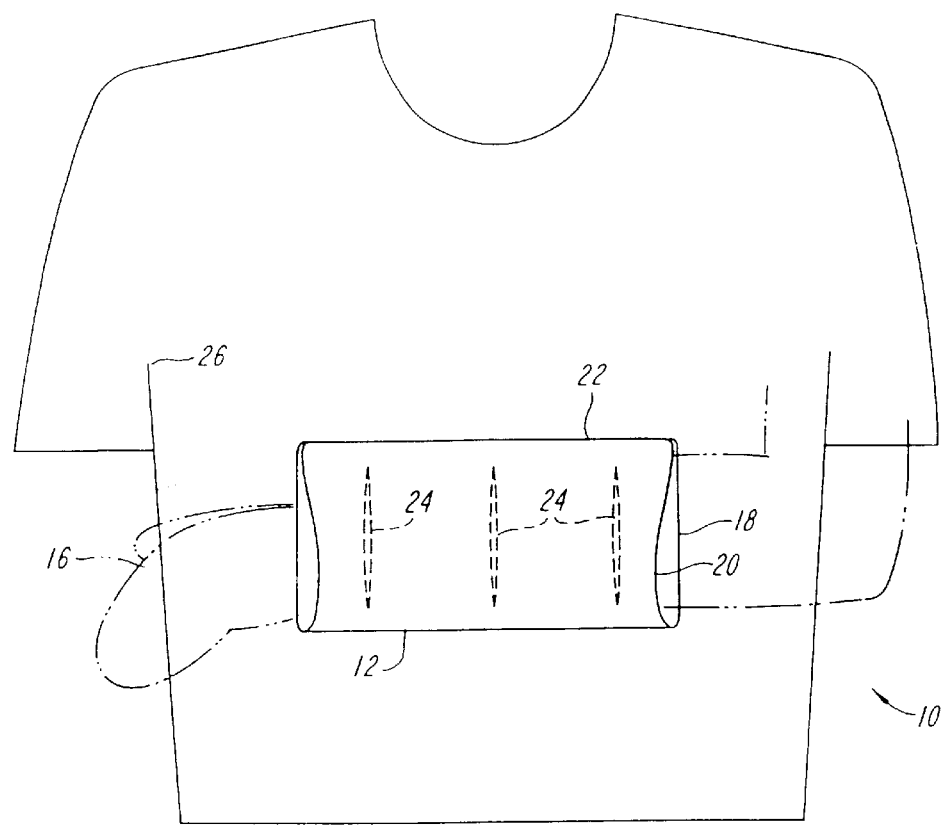
FIG. 2 is a perspective view of the interior of the arm support garment of FIG. 1 showing an integrally placed arm support pouch.

Referring to FIGS. 1 and 2, the arm support garment of the invention 10 includes an integral sling pouch 12 incorporated on the inside of the garment, and accessible, from the outside of the garment, through vertical slits 14 near each end of the pouch, for supporting an injured upper extremity 16. The sling pouch consist of one or more panels 18, 20 of preferably double layers of cotton cloth, or similar fabric material.

When the pouch is made of two panels, the first panel 18, closest to the inner surface of the front of the garment, is either an integral part of the garment or is sewn on to the inner surface of the garment. The second panel 20, further away from the inner wall of the front of the garment, is secured at its lower and upper edges by sewing, or any other means, to the edges of the first panel, and/or to the wall of the garment. The upper edge 22 of the second panel may be left open, although it is preferable to close it. The length of the panels ranges from, e.g., seven to twenty inches, to accommodate a wide range of forearm lengths, and to allow the use of vertical ventilating slits 24 in the panels. The width of the panels ranges between, e.g., three and eight inches to allow for placement of different diameter extremities.

Figure 3:
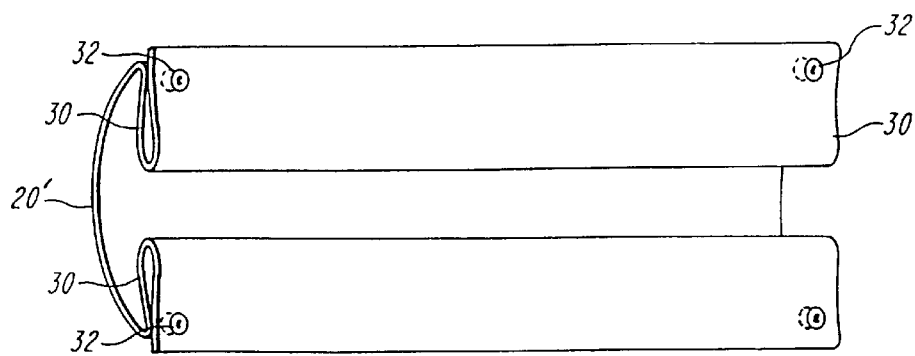
FIG. 3 is a plan view of the arm support pouch of FIG. 2 showing a multiply folded segment.

The support pouch can be made to be expandable. Referring also to FIG. 3, in another embodiment, second panel 20', viewed from the inside of the support pouch, preferably has one or more folded segments 30, adjacent to the upper and lower edges of panel 20', which are secured with a snap grommet or Velcro tab 32, or by any similar means. The folded segment can be released to give a greater girth or volume to the space enclosed by the two panels in order to accommodate an extremity that may be bearing a cast. In this configuration, such a support pouch can also be used with traditional arm slings, as it allows a single sleeve to accommodate medium, large, and extra large sized extremities.

Referring again to FIGS. 1 and 2, it can be seen that the support pouch panels 18, 20 are positioned at an optimum level to allow easy insertion of an arm 16, through slits 14, into the enclosure formed by the panels. This position is typically between one and three inches below the level of the lower seam 26 of the sleeve attachment. The panels are also positioned symmetrically in the central section of the garment to provide easy access and use by either the left or the right upper extremities. The distance between the lateral edges of the panels and the side seams of the garment could range from one to five inches depending on the length of the extremity and the size of the garment.

The arm support garment of the invention can be reversed as it is a dual surface outfit. The design of a reversible garment will be compatible with design modifications existing currently in the fashion industry. Reversing the garment will also allow the second panel on the inside to be exposed for use as an exteriorly positioned sling. This would be particularly useful in hot and humid weather.

The two panels 18 and 20, and the front surface of the garment 10 itself in the case of an integral first panel, are provided with multiple slit openings 24 that run from the upper borders to the lower borders of the panels. Preferably, these vertical slits, e.g., from two to four in number, are placed in each panel 18, 20 and spaced from one to three inches apart to minimize a tendency to tear. The first and the last of this vertical slit openings in inner panel 18 coincide with access window 14 for insertion of either the right, or the left arm. The position of these vertical slits may, or may not, be at the same level in the two panels of the garment. The vertical slits serve two purposes. First, they serve as vents to ensure good air circulation to the inner aspect of the garment. Secondly, they serve as variable access windows for insertion of the forearm into the enclosed inner pouch. In other words, when the most lateral vertical slit is not suitable for a particular individual, the forearm can be inserted into the next slit in line. This flexibility permits a large size garment to be worn by someone with a fairly short forearm.

The material between the vertical slits is further reinforced by sewing the two layers constituting the panels, or, if preferred, by interposing additional layers of reinforcing material. The amount of material between the vertical slits is also such that it can withstand tensile stresses greater than 2 Newton per square meter exerted by the upper extremity and not tear. Also, as the overall weight is shared uniformly along the length of the pouch, this further limits the tensile stress on individual strips of cloth between the vertical slits.

The opposing edges of each vertical slit can be securely closed if desired by attaching a securing means in the form of Velcro tags, snap-on grommets, or any other attachment means. This is important as this garment can be converted to regular clothing after it has served its therapeutic purpose. By closing off the vertical slits, the patient may convert the enclosure to a form of pocket that may hold light material objects. It also allows for sealing of the exteriorly connecting vertical slits when the weather is cold.

Figure 4:
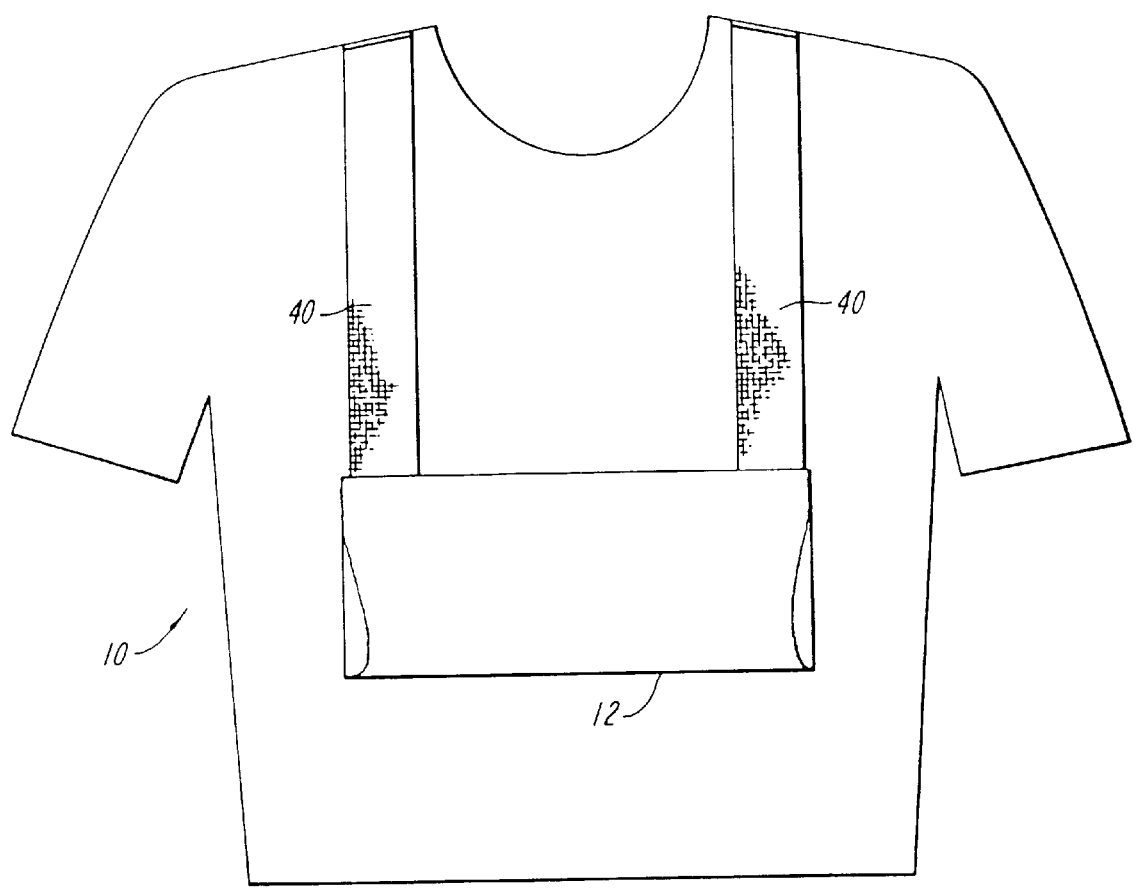
FIG. 4 is a perspective view of the interior of the front portion of an alternate embodiment of the arm support garment of the invention showing an integral strap support.
Figure 5:
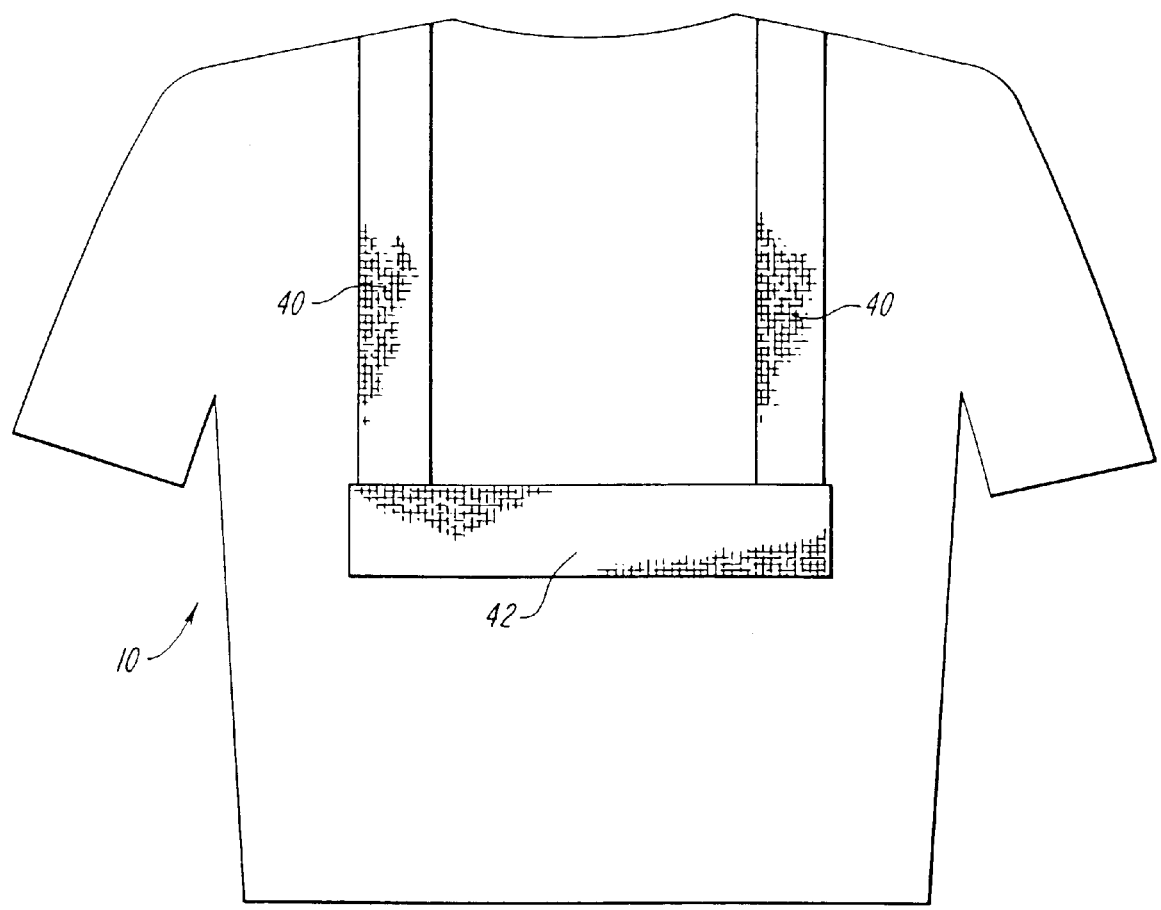
FIG. 5 is a perspective view of the interior of the rear portion of the support garment of FIG. 4.

Referring now to FIG. 4, in an alternate embodiment, on the inner aspect of both the front and back portions of support garment 10, narrow strips of strap-like cloth 40 are either sewn in separately, or manufactured as an integral part of the garment itself. These straps are on either side of the garment and run from the superior aspect of panels 18, 20 over the shoulder of the garment and end at any level on the inner surface of the back of garment 10, ranging from the superior seams of the garment to the lower edge of the garment. Referring to FIG. 5, on the inner wall of the back of the garment, straps 40 may be connected for additional strength by, e.g., a transversely running strap 42 of similar or greater size. Alternatively, straps 40 may, e.g., be crossed. These strap-like modifications, preferably manufactured as an integral part of the clothing, further strengthen the garment to withstand any tensile stresses that may be generated by the weight of a suspended upper extremity. This modification is preferred in garments for large individuals but may not be necessary, particularly for small sized individuals, as the secured pouch alone should withstand the weight of the extremity.

Figure 6:
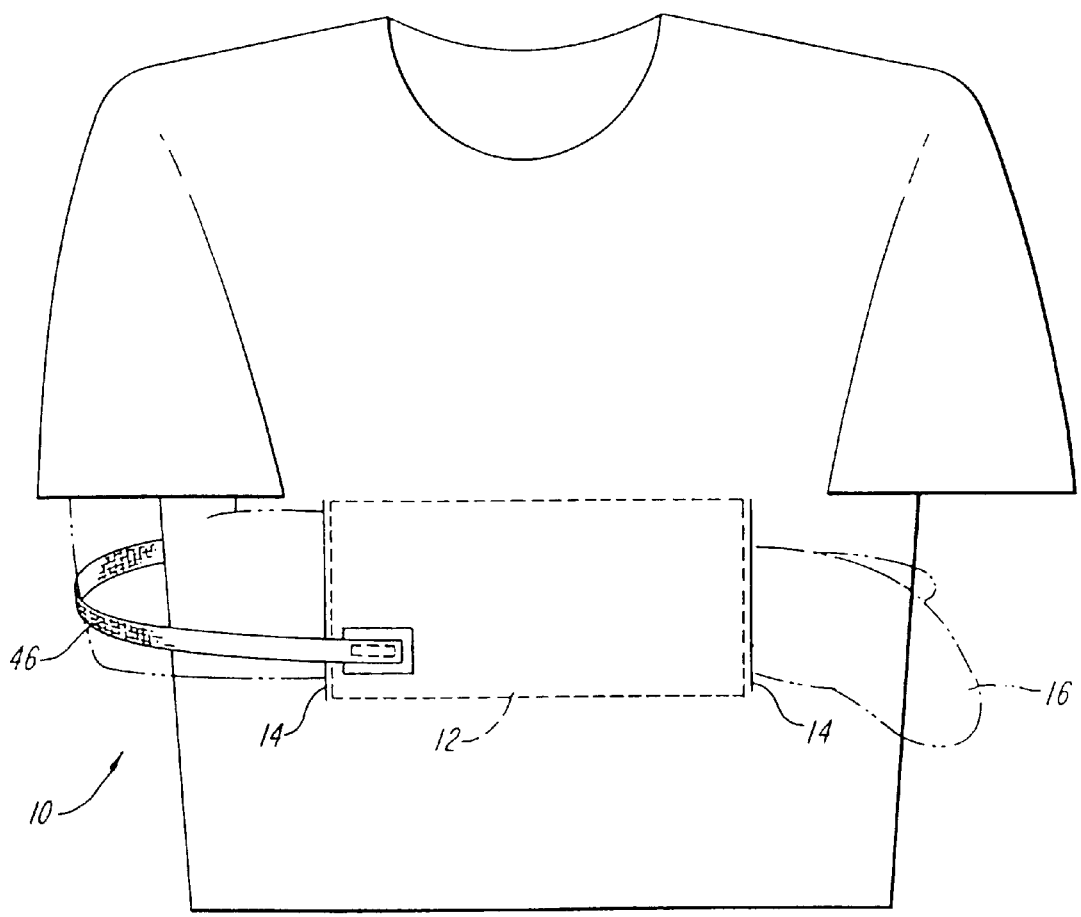
FIG. 6 is a perspective view of an alternate embodiment of the arm support garment of the invention showing an optional accessory restraining strap and attachment.

Additional accessories can be added to the arm support garment as completely detachable attachments, which may be necessary for a selected number of patients. Referring to FIG. 6, such accessories include a restraining strap 46 that can be attached to the exterior surface of the garment to secure the exposed elbow of the enclosed forearm in the pouch and prevent it from sliding outward. Strap 46 can be fixed to the rear of the garment (permanently or detachably) on the side where needed, placed around the patient's elbow and secured in the front of the garment, e.g., near the vertical slit bearing the extremity, and secured by using a snap-on button, Velcro, or any other attachment means. This restraining strap can be applied either to the standard form of use of this garment or to the reversed form of this garment.

The sizing of the arm support garment ranges from the petite size to an extra-large size in consistence with established standardized sizing dimensions. The garment can be worn as a primary garment, or as over clothing. When the garment is worn over other clothing, the appropriate sizes will be larger than those that the individual normally wears.

The arm support garment of the invention can be in the form, e.g., of a shirt, T-shirt, jacket or a gown with necessary modifications to allow for this invention. The color and design can be those of any textiles selected by the manufacturer.

The choice of material for the arm support garment is such that it can withstand mechanical deformation in the form of twisting, stretching, shearing, and abrasion. The material used should have a reasonable tensile strength (over a relatively wide temperature, particularly with washing) and a high modulus of elasticity, as well as abrasion resistance, particularly when used with an extremity bearing a cast. Cotton or surgical fiber fabric material, or any other material or combination of materials that satisfy one or more of these criteria, may be used for the purpose of this invention. Textile design modifications in line with current practice will be necessary to make this garment wearable in its reversed form.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. An arm support device comprising an article of clothing to be worn on the trunk of a patient in need of arm support, said article having a front portion, a back portion and a shoulder portion, each said portion of said article having an interior surface and an exterior surface and each of said front, back and shoulder portions being integrally connected to the other two of said portions, said front back and shoulder article comprising an integrally connected support pouch for said arm attached to the interior surface of said front portion of said article of clothing, said article further comprising one or more slits in said front portion in transverse orientation to the primary axis of said pouch, said slits extending from the exterior surface of said front portion through said front portion and a wall of said support pouch to the interior of said support pouch, wherein said slits provide access through said front portion to said support pouch for said patient in need of arm support.

2. The arm support device of claim 1, wherein said support pouch for said arm is expandable in width along the length of the pouch.

3. The arm support device of claim 1, further comprising an interior support strap or straps extending from said support pouch to the shoulder area of said garment.

4. The arm support device of claim 1, wherein said interior and exterior surfaces of said portions of said article of clothing are esthetically configured to be reversible.

5. The arm support device of claim 1, wherein said article is made from a material having limited stretch capacity.

6. The arm support device of claim 1, further comprising a restraining strap or straps.

7. An expandable arm support pouch for attaching to an orthopedic arm sling, said pouch comprising a material configured as an enclosed sleeve having an open anterior end, an open posterior end and an axis extending from said anterior to said posterior ends, wherein a portion of said pouch material along said axis is folded along said axis and secured in place along said axis so that said pouch is expandable in width along its length, said pouch also being configured as an enclosed sleeve when expanded, said pouch further comprising a fastening device for attaching said pouch to an orthopedic arm sling.

* * * * *